(12) United States Patent
Scheer et al.

(10) Patent No.: US 8,388,994 B1
(45) Date of Patent: Mar. 5, 2013

(54) FIBROUS NON-WOVEN POLYMERIC MATERIAL

(76) Inventors: Ingo Scheer, La Jolla, CA (US);
Claudia Beaumont, San Diego, CA (US)

( * ) Notice: Subject to any disclaimer, the term of this patent is extended or adjusted under 35 U.S.C. 154(b) by 731 days.

(21) Appl. No.: 12/481,189

(22) Filed: Jun. 9, 2009

Related U.S. Application Data

(60) Provisional application No. 61/060,106, filed on Jun. 9, 2008.

(51) Int. Cl.
| | |
|---|---|
| *A61F 2/00* | (2006.01) |
| *A61F 2/02* | (2006.01) |
| *A61F 2/04* | (2006.01) |
| *A61K 9/70* | (2006.01) |
| *A61L 33/00* | (2006.01) |
| *B05D 3/00* | (2006.01) |
| *B05D 1/02* | (2006.01) |
| *C12N 11/10* | (2006.01) |
| *C12N 11/08* | (2006.01) |

(52) U.S. Cl. ........ 424/423; 424/425; 424/426; 424/443; 424/444; 424/484; 424/486; 424/488; 424/93.7; 427/2.1; 427/2.24; 427/2.25; 427/421.1; 435/178; 435/180

(58) Field of Classification Search ................... None
See application file for complete search history.

(56) References Cited

U.S. PATENT DOCUMENTS

| 7,504,060 B2 * | 3/2009 | Brock et al. ................. 264/465 |
| 7,892,593 B2 * | 2/2011 | Scheer ........................... 427/2.1 |
| 2005/0064168 A1 * | 3/2005 | Dvorsky et al. ............. 428/292.1 |
| 2007/0043428 A1 * | 2/2007 | Jennings et al. ............. 623/1.15 |

* cited by examiner

*Primary Examiner* — David M Naff

(57) ABSTRACT

The present invention relates to biocompatible non-woven fibrous materials having a nano-micro topography and methods for producing such materials. The materials may be used to cover implantable medical devices and to fabricate a three-dimensional drug-eluting fibrous matrix featuring accurate spatial positioning of the drug particles within the matrix.

19 Claims, 12 Drawing Sheets

FIBROUS NON-WOVEN POLYMERIC MATERIAL

CROSS-REFERENCE TO RELATED APPLICATIONS

This Application relates to and claims priority from U.S. 61/060,106 filed Jun. 9, 2008, which is incorporated as reference herein.

FEDERALLY SPONSORED RESEARCH

Not Applicable

SEQUENCE LISTING OR PROGRAM

Not Applicable

BACKGROUND OF THE INVENTION

The present invention relates to biocompatible non-woven fibrous materials having a nano-micro topography, which may be used to cover implantable medical devices and to fabricate three-dimensional drug-eluting materials, and methods for producing such materials.

Non-woven materials made from synthetic or natural polymers are used in various applications, including tissue engineering, clinical diagnostics, wound healing, drug delivery, and medical implants. Such materials may be employed, among others, to produce vascular grafts for supporting a weakened artery and covered stents which inhibit tissue growth into the stents. Vascular grafts and covered stents generally consist of a support structure and a cover surrounding it. The support structure is typically a mesh cylindrical device that fits into the opened artery and is radially expanded against the walls of the artery.

It is known to fabricate non-woven materials using a process by which polymer fibers are produced by means of an electrostatically driven jet of polymer solution, referred to as electrospinning. Electrospinning is however a rather complex and time-consuming manufacturing process, which requires applying a high voltage and provides insufficient control of material homogeneity and reproducibility. In particular when small fibers, such as nanosize fibers, are produced the total yield of the electrospinning process is very low and process scale-up cannot be easily achieved. FIG. 1A represents a scanning electron microscopy (SEM) image of a portion of an electrospun material known by the prior art, which has been analyzed to obtain quantitative information on the surface features. Referring to FIG. 1B, it can be seen that the material is comprised of long spaghetti-like fibers having various thicknesses of about one to four microns and has a rather inhomogeneously randomized pattern with pores ranging from one to twelve microns.

Since implantable medical devices will often provoke adverse body reactions, a therapeutic agent may be applied to the devices to improve the biocompatibility and/or treat diseases by delivering the therapeutic agent directly to the target site. However, incorporation of drugs into the polymer will not ensure a controlled drug distribution as schematically visualized in FIG. 2. A therapeutic agent 137 may not be homogeneously distributed within a composition 126 comprising one or more polymers 140 and therapeutic agents 137 due to particle sedimentation, particle aggregation, and the like. This can result in an inhomogeneous distribution of the therapeutic agent within the produced material and may have a negative impact on the performance of the specific drug delivery product.

OBJECT OF THE INVENTION

To overcome the limitations of the prior art a new process is provided to produce non-woven biocompatible fibrous materials (structures or membranes) having nano-micro sized features, which are substantially homogenous and tunable in terms of elasticity, porosity, permeability, and rigidity.

One object is to provide a new and flexible approach to fabricate fibrous membranes having a homogeneous thickness with improved biocompatibility and reproducibility, especially tubular membranes suitable for small diameter vascular prostheses and covered stents.

A further object is to provide a versatile and gentle process with the ability to incorporate multiple polymers and beneficial agents without prolonged drying intervals to enhance mechanical properties, material biocompatibility and allow localized drug delivery of high molecular weight and temperature sensitive drugs.

Another object is to control the membrane structure at the nano- and micro-scale to enhance its biomimicity, such as to promote morphological similarities to the three-dimensional extracellular matrix (ECM).

Yet another object is to provide a stent covered with a multi-layered nano-micro textured drug-eluting membrane.

Still another object is to provide a three-dimensional drug-eluting polymeric matrix for spatially controlled drug positioning and release of multiple drugs.

These and additional features and advantages of the invention will be more readily apparent upon reading the following description of exemplary embodiments of the invention and upon reference to the accompanying drawings herein.

SUMMARY OF THE INVENTION

In one embodiment, a method to form a fibrous structure is provided. It comprises the steps of: providing an atomizing device for supplying at least a liquid composition including at least a volatile component and at least a non-volatile component; providing a substrate at a determined position from the atomizing device; atomizing the liquid composition using a gas stream and forming simultaneously a plurality of fibers from the non-volatile component having a size ranging between 15 and 500 microns; and depositing the fibers on the substrate so that a mesh-like structure composed of a plurality of interconnected short fibers is formed that covers at least a part of the surface of the substrate.

In one or more embodiments, the method further comprises the step of inducing swirl motion into the atomizing gas stream to fine-tune the inclination and orientation of the fibers. The velocity of the atomizing gas may exceed sonic speed and at least 20% of the droplets formed from the volatile component may be submicron sized. The method can further comprise the step of providing an additional gas stream to increase the temperature of the atomizing gas stream to a temperature higher than ambient temperature. In addition, the step of applying an electrical charge to the liquid composition to fine-tune the deposition of the fibers may be provided. The non-volatile component preferably comprises a polymeric substance and the liquid composition a therapeutic agent. The substrate may be a scaffold and the fibrous structure may be removed from the scaffold. Alternatively, the substrate can be a tissue of a living body on which the fibrous structure is formed in situ to cover at least a part of the tissue surface. Also, the substrate may be a medical device and the fibrous structure may cover at least a part of the medical device. The method may further comprise the step of applying a therapeutic agent using an additional atomizing device after the solidification of the polymeric component is initiated to allow spatially defined embedding of the therapeutic agent into the fibrous structure.

In a further embodiment, a fibrous non-woven polymeric membrane is provided. The membrane comprises a mesh-like three-dimensional structure with homogenously distributed surface features in the nano-micrometer range and is composed of a myriad of closely interconnected short fibers, being inclined with respect to each other, having a size between 15 to 500 microns and a diameter in the nano-micrometer range.

In one or more embodiments, the membrane is manufactured using a pneumatic spraying process. The membrane can be formed in situ and cover at least a part of the tissue surface of a living body. Alternatively, the membrane may cover at least a part of a medical implant, such as a stent, consisting of an expandable tubular hollow mesh structure. In addition, the membrane may form a vascular graft having a tubular hollow body and may mimic the size scales of fibers composing the extracellular matrix. The membrane is preferably biodegradable and may comprise multiple layers in which one or more therapeutic agents are embedded in a defined position.

BRIEF DESCRIPTION OF THE SEVERAL VIEWS OF THE DRAWINGS

The accompanying drawings, which are incorporated herein and form a part of the specification, illustrate the embodiments of the present invention and together with the description, serve to explain the principles of the invention. In the drawings.

DETAILED DESCRIPTION

Figure 1A:
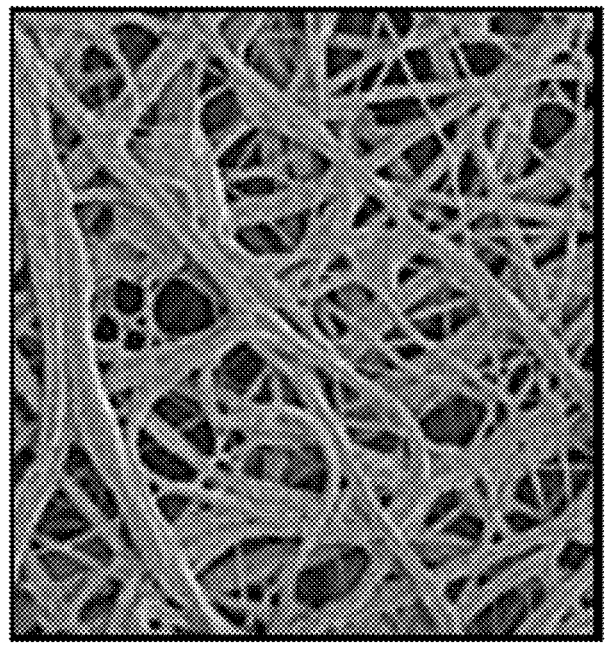
FIG. 1A is a SEM image of a portion of an electrospun membrane (Prior Art)
Figure 1B:
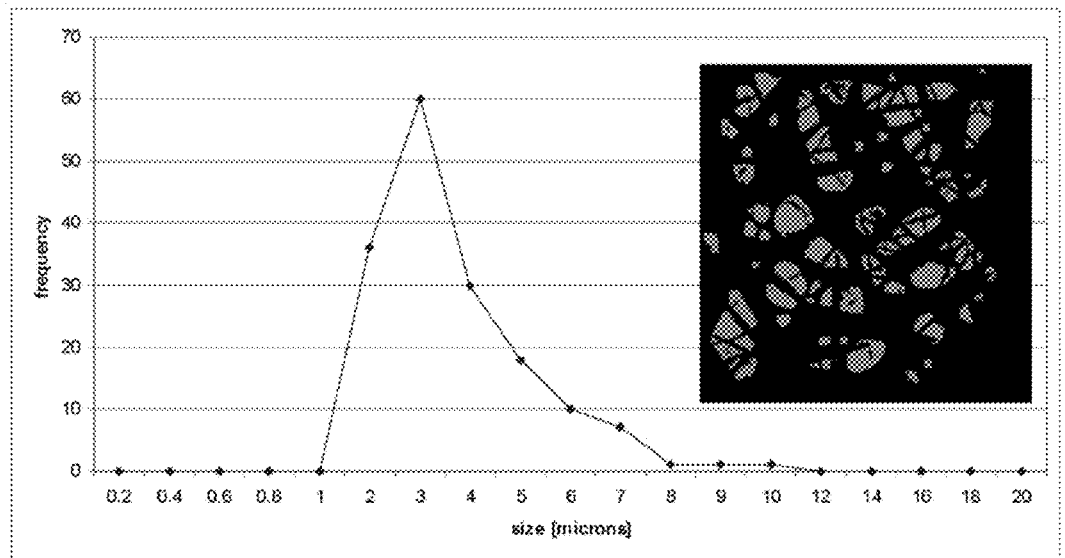
FIG. 1B is a surface feature analysis of FIG. 1A (Prior Art)
Figure 2:
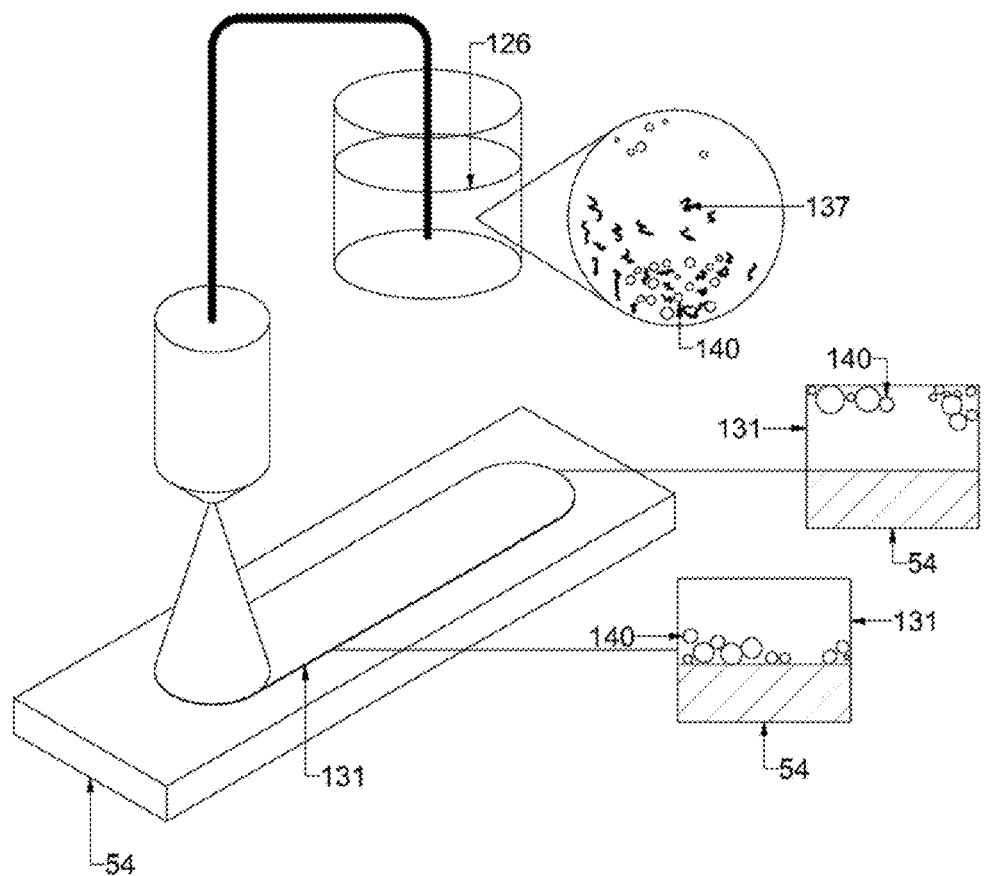
FIG. 2 is a conventional process to fabricate a drug-eluting polymer matrix (Prior Art)

Further aspects of the invention will become apparent from consideration of the drawings and the ensuing description of preferred embodiments of the invention. Thus, the following drawings and description are to be regarded as illustrative in nature and not restrictive. A method for covering a cardiac stent is used as the model for description of the method of the present invention. Use of the medical stent model is not intended to limit the applicability of the method to that field. It is anticipated that the invention can be successfully utilized in other circumstances such as to fabricate a vascular prosthesis, particularly a synthetic blood vessel, various tubes or various kinds of artificial ducts, such as urinary, air or bile ducts. In addition, the present invention may be used for producing tissues like medical meshes that may be implanted or applied to a human or animal body. The present invention may also be employed for the treatment of burn wounds by spraying a healing membrane directly on the skin of a human or animal body.

The method of forming a thin non-woven fibrous structure comprises the following steps: providing an atomizing device for supplying at least a liquid composition including at least a volatile component and a non-volatile component; providing a substrate at a determined position from the atomizing device; atomizing the liquid composition using a gas stream and forming simultaneously a plurality of fibers from the non-volatile component having a size ranging between 15 and 500 microns; and depositing the fibers on the substrate so that a mesh-like structure of interconnected fibers is formed that covers at least a part of the surface of the substrate.

The substrate may be made from a solid tubular or flat material, but is preferably a mesh structure. It can be furthermore composed of a plurality of wires or rods arranged in parallel, which may be hold in a fixed position by a frame.

The substrate may be used only during the manufacturing process to produce a self-supporting scaffold for cell growing and/or implantation in a human or animal body, for fabricating synthetic vascular grafts or various drug delivery devices. It should be therefore easily removable and preferably made from or coated with a non-stick material, such as Teflon. Alternatively, the substrate may be part of a prosthesis implanted in a human or animal body, such as a stent graft or a balloon-expandable and self-expandable covered stent. Balloon-expandable stents are mounted over a balloon catheter to expand the stent to a larger diameter due to plastic deformation of its struts. In the self-expandable design, the stent is typically covered with a constraining sheath, which is released to elastically expand the stent. The material creating the stent (substrate) should be flexible, sufficiently rigid to provide support and capable of homogeneous expansion. It is important to ensure that the material is biocompatible and does not leave harmful substances in the body. Suitable metallic materials include, among others, 316L stainless steel, gold, tantalum, cobalt-chromium alloy, and shape memory alloys such as Nitinol. Polymer materials comprise, among others, biostable materials like silicone and polyurethane, biodegradable materials, and shape-memory polymers with structural flexibility and shape variability.

The mesh structure of the stent should ensure symmetric expansion, sufficient stability and a low profile. It may be constructed, among others, by casting or by weaving strands of metal wire into coils, cutting patterns into thin metal tubes using lasers, cutting patterns into thin metal sheets followed by rolling into tubes and welding, and by welding together multiple links cut from metal tubing.

The polymeric component used to fabricate the fibrous membrane or structure should have a sufficiently high molecular weight, glass transition temperature and concentration to allow formation of fibers in a determined size range. The strength and elasticity of the membrane is influenced by the orientation and interconnection of the fibers, the mechanical characteristics of the polymer being used, and the geometrical size and form of the fibers. For example, if used as a scaffold for tissue engineering, the fibrous structure may be manufactured from a wide variety of biodegradable and biocompatible polymers including synthetic polymers, such as poly(lactide), poly(glycolide) and their copolymers (PLGA), poly(e-caprolactone) (PCL), poly(ethylene-co-vinyl alcohol), and natural polymers, such as collagen, protein and fibrinogen. Biomaterials, which may be used to fabricate grafts or other devices to regenerate lesions in other tissues like skin and bone, include, among others, poly(phosphoester), polyethylene, silicon, polytetrafluoroethylene, collagen, polyglycolide, collagen and poly-glycolide, poly(L-lactide-co-glycolide) (PLGA), and poly-L-lactic acid/caprolactone.

Depending on the application one or more of the following components may be used to construct the fibrous membrane or structure: 1) synthetic polymers including polyethylen (PE), poly(ethylene terephthalate), polyalkylene terepthalates such as poly(ethylene terephthalate) (PET), polycarbonates (PC), polyvinyl halides such as poly(vinyl chloride) (PVC), polyamides (PA), poly(tetrafluoroethylene) (PTFE), poly(methyl methacrylate) (PMMA), polysiloxanes, ethylene-vinyl acetate (EVAc), polyurethane polysiloxanes, and poly(vinylidene fluoride) (PVDF); 2) biodegradable polymers such as poly(glycolide) (PGA), poly(lactide) (PLA), poly(anhydrides) poly(lactic-co-glycolic acid) (PLGA), PEG-PLA-PEG, PEG-PLGA-PEG, PEG-PCL-PEG, PLA-PEG-PLA, PHB, P(PF-co-EG) tacrylateend groups, P(PEG/PBO terephthalate), PEG-bis-(PLA-acrylate), PEG6CDs, PEG-g-P(AAm-co-Vamine), PAAm, P(NIPAAm-co-AAc), P(NIPAAm-co-EMA), PVAc/PVA, PNVP, P(MMA-co-HEMA), P(AN-co-allylsulfonate), P(biscarboxy-phenoxy-phosphazene), P(GEMA-sulfate); 3) natural polymers and their derivatives including HA, alginic acid, pectin, carrageenan, chondroitin sulfate, dextrane, sulfate, chitosan, polylysine, collagen, gelatin, carboxymethyl chitin, chitosan, fibrin, collagen, dextran, agarose, pullulan, sclerogluan, cellulose, albumin, silk; 4) combinations of natural and synthetic polymers including P(PEG-co-peptides), alginate-g-(PEO-PPO-PEO), P(PLGA-co-serine), collagen-acrylate, alginate-acrylate, P(HPMA-g-peptide), P(HEMA/Matrigel), HA-g-g-NIPAA; and 5) mineral, vegetable or animal oils may be also included such as fish oil, cod-liver oil, olive oil, linseed oil, sunflower oil, corn oil, and/or palm oil.

The fibrous material can comprise one or more beneficial agents or drugs that may be released over time, if the release of a large amount of drug (burst released) within a short time window is not desired. The drug release can be influenced, among others, by the molecular size of the drug, its crystallinity and hydrophil/lipophil balance, the morphology, hydrophilicity/hydrophobicity and glass transition point (Tg) of the fibrous material forming a three-dimensional matrix, the thickness (number of layers) of the matrix, and the distribution of the drug within the matrix.

The term "beneficial agent", as used herein, is intended to have its broadest possible interpretation and is used to include any therapeutic substance, active agent or drug hat is delivered to the body of a living being to produce a desired beneficial effect. It may include, but is not limited to proteins, hormones, vitamins, anti-microbacterial agents, antioxidants, DNA, antimetabolite agents, anti-inflammatory agents, anti-restenosis agents, anti-thrombogenic agents, antibiotics, anti-platelet agents, anti-clotting agents, chelating agents, or antibodies. Specific examples include hyaluronic acid (HA), omega-3 fatty acids (DHA/EPA), acetylsalicylic acid, dexamethasone, M-prednisole, interferon y-1b, Leflunomide, sirolimus, tacrolimus, everolimus, mizoribine, ABT-578, QP-2, actinomycin, methothrexate, angiopeptin, vincristine, mitomycine, statins, PCNA Ribozyne, Batimastat, Prolyl hydroxylase inhibitors, C-proteinase inhibitors, Probucol, Re-Endothelialization, BCP671, VEGF Estradiols, NO donors, EPC antibodies; antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative agents such as paclitaxel, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine; antimicrobials such as triclosan, cephalosporins, aminoglycosides, nitorfurantoin, 2,4,4'-trichloro-2'-hydroxydiphenyl ether; silver zeolite or silver glass; 4-t-butylamino-6-cyclopropylamino-2-methylthio-s-triazine, CAS No. 28159-98-0; thiabendazole, 2-(4-thiazolyl)benzimidazole, CAS No. 148-79-8; dichloro-octyl-isothiazolone; octyl-isothiazolone; 10,10-oxybisphenoxarsine; tebuconazole; tolnaftate; and zinc bis-(2-pyridinethiol-1-oxide); anesthetic agents such as lidocaine, bupivacaine, and ropivacaine; anti-coagulants such as D-Phe-Pro-Arg chloromethyl ketone, heparin, antithrombin compounds, anti-thrombin antibodies, anti-platelet receptor antibodies, aspirin, prostaglandin inhibitors, platelet inhibitors; vascular cell growth promoters such as growth factors, growth factor receptor antagonists, transcriptional activators, and translational promoters; vascular cell growth inhibitors such as growth factor inhibitors, growth factor receptor antagonists; transcriptional repressors, translational repressors, replication inhibitors, inhibitory antibodies, antibodies directed against growth factors; and cholesterol-lowering agents. Cells that may be introduced onto a tissue substrate include, without limitation, keratinocytes, fibroblasts, hepatocytes, pancreatic cells, lung cells, muscle cells (smooth, cardiac, striated), chondrocytes, osteoblasts, endothelial cells, fertilized ova, adrenal cells, and neurones.

The volatile component or solvent used for dissolving the polymeric component and the therapeutic substance is selected based on the solubility of the material to be dissolved as well as on its biocompatibility, surface tension and vapor pressure. The solvent should be sufficiently fast evaporating and have a boiling point below 90 degree C. It may perform a variety of functions including dissolving polymers and other non-volatile materials, reducing viscosity, and providing a carrier medium for dispersions. Generally the solvent is at least partially miscible with the non-volatile material. The selection of a particular solvent for a given non-volatile material to obtain desired solubility and dispersibility characteristics is known to those skilled in the art. Aqueous solvents can be used to dissolve water-soluble materials, such as Poly (ethylene glycol) (PEG) and organic solvents may be selected to dissolve hydrophobic and some hydrophilic materials.

Examples of suitable solvents include methylene chloride, ethyl acetate, ethanol, methanol, dimethyl formamide (DMF), acetone, acetonitrile, tetrahydrofuran (THF), acetic acid, dimethyle sulfoxide (DMSO), toluene, benzene, acids, butanone, water, hexane, and chloroform, N-methylpyrrolidone (NMP), 1,1,2-trichloroethane (TCE), various freons, dioxane, ethyl acetate, cyclohexanone, and dimethylacetamide (DMAC). For the sake of brevity, the term solvent is used to refer to any fluid dispersion medium whether a solvent of a solution or the fluid base of a suspension.

Figure 3:
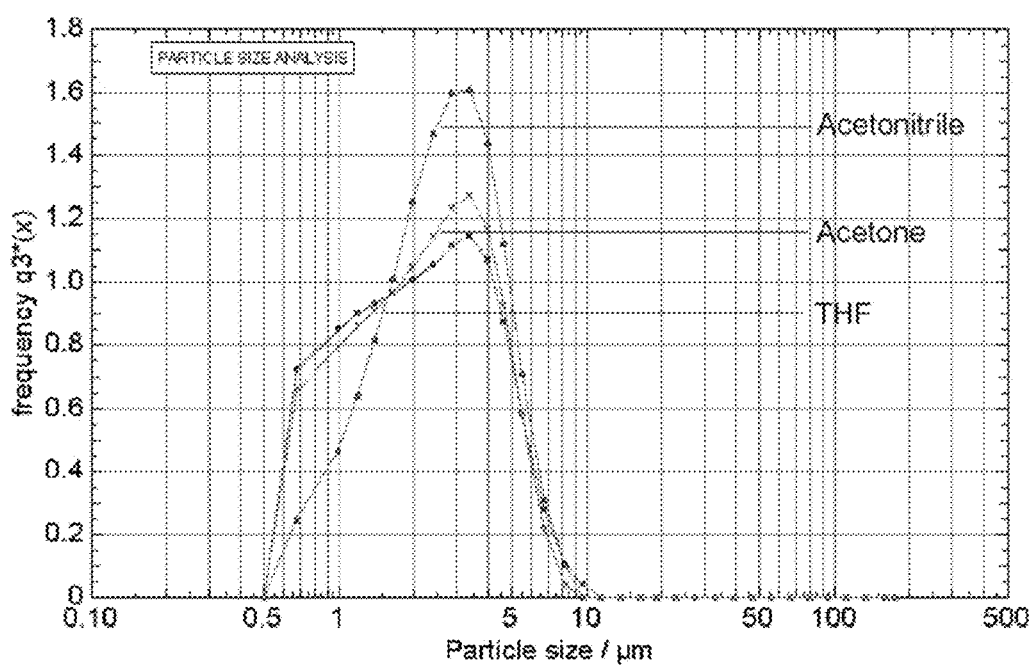
FIG. 3 is a droplet size distribution comparison of different solvents.

It is an important feature of the present invention to ensure satisfactory solvent evaporation and controlled fiber formation. This requires that the volatile component of the composition is disintegrated into fine droplets at atomizing pressures of preferably less than 2.5 bar. FIG. 3 represents a droplet size distribution comparison for Acetonitrile (vapor pressure: approx. 80 mmHg at 20 degree C.), Tetrahydrofuran (vapor pressure: approx. 143 mmHg at 20 degree C.) and Acetone (vapor pressure: approx. 180 mmHg at 20 degree C.). The droplet size of three organic solvents was measured using a Fraunhofer diffraction system (Sympatec, Lawrenceville, USA) at room temperature (about 20 degree C.) and at a relative humidity of 60%. A volumetric median diameter (VMD) of approximately 3 microns at an atomizing pressure of less than 1.5 bar was obtained for the tested organic solvents. The comparatively small droplet sizes lead to an increased evaporation rate or volatility of the solvent due to the increased vapor pressure, which most significantly augments for droplet sizes below 4 microns and in an exponential manner for sub-micron sized droplets.

Figure 4:
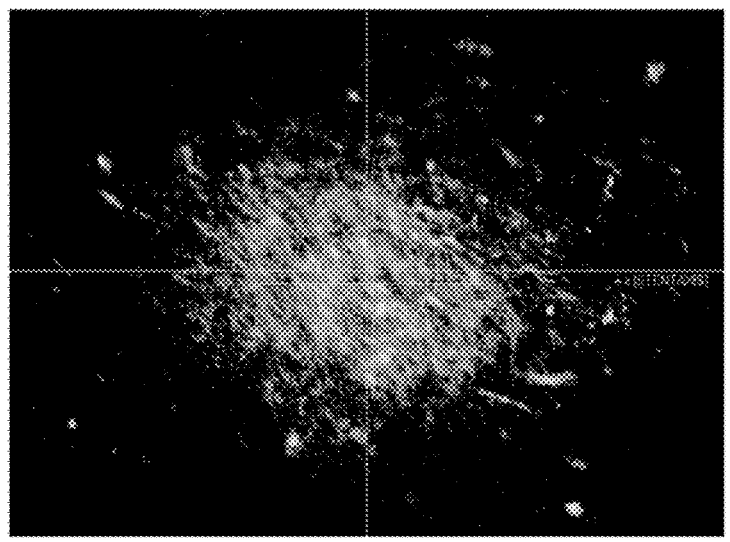
FIG. 4 is a screenshot visualizing polymer fibers.
Figure 5:
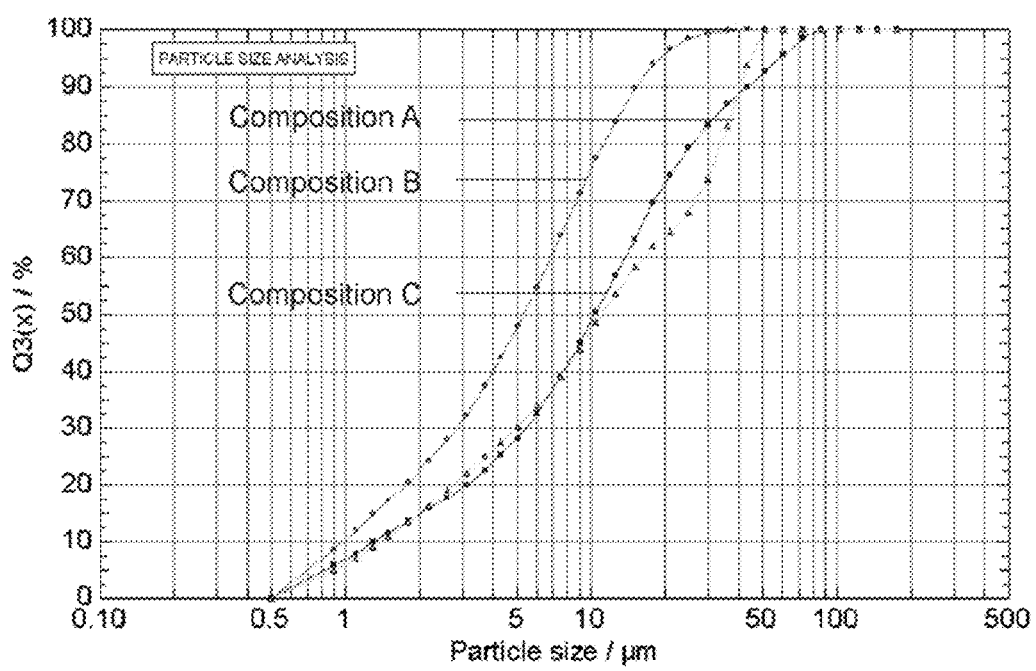
FIG. 5 is a size distribution comparison of polymer fibers.

FIG. 4 shows polymer fibers produced according to the method of the present invention, which may be formed from a wide variety of biodegradable and biostable polymeric compositions. The size distribution of the fibers for three exemplary polymer compositions is depicted in FIG. 5. Composition A was prepared with the polymeric components poly(lactide co glucolide) and poly(ethylene glycol) dissolved in acetone, composition B was composed of poly(ethylene co vinyl acetate) dissolved in tetrahydrofuran and composition C was prepared using Polyurethane dissolved in tetrahydrofuran. The fiber size distribution was measured using a Fraunhofer diffraction system (Sympatec, Lawrenceville, USA). Referring to FIG. 5, the fibers produced from composition C have a high distribution density in the 10 to 40 micron size range. The median fiber size is around 17 microns and approximately 36% of all fibers are larger than 15 microns. Composition A has a high distribution density at about 50 microns. The median fiber size is around 17 microns and approximately 42% of all fibers are larger than 15 microns. For composition B the fibers have a high distribution density at around 10 microns. The median fiber size is approximately 7 microns and approximately 10% of all fibers are larger than 15 microns.

Figure 6A:
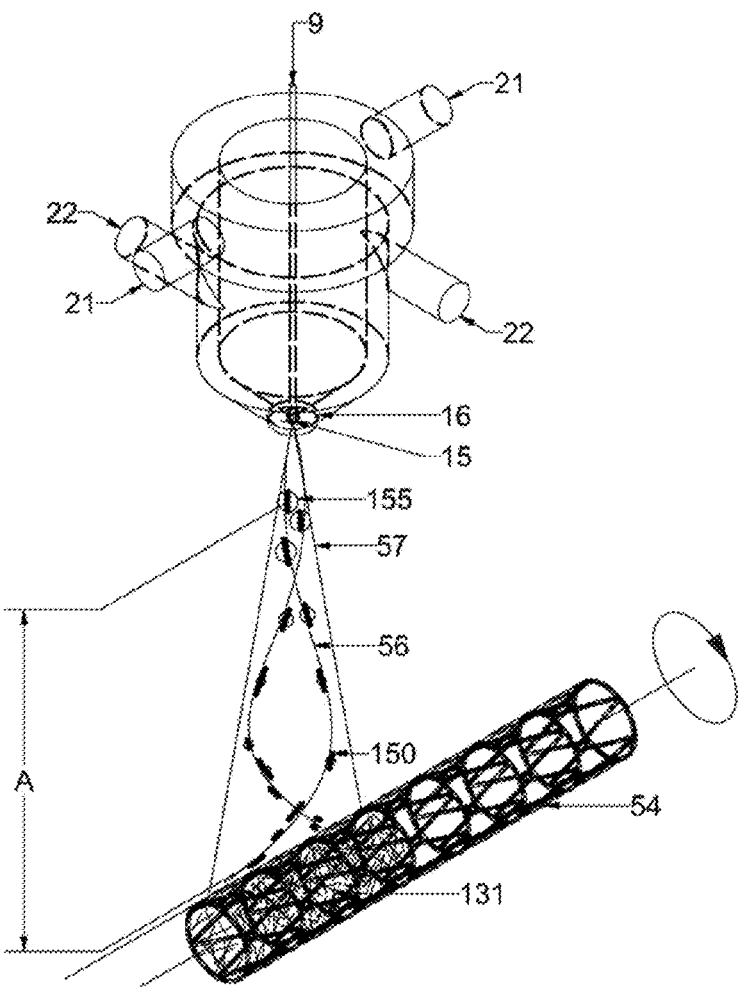
FIG. 6A is a schematic representation of the fabrication method of the fibrous material of the present invention.

An exemplary setup for the fabrication of a nano-micro textured fibrous structures according to the method of the present invention is schematically shown in FIG. 6A. The composition to be disintegrated may be supplied as a solution, emulsion, dispersion, or suspension. It may include one or more polymers, beneficial agents, oils, and/or fats. In addition plasticizers to reduce the glass transition temperature, buffers to adjust the pH of the composition, surfactants to enhance the wettability of poorly soluble or hydrophobic materials, radiopaque elements, radioactive isotopes may be comprised. With reference to FIG. 6A, a substrate (tubular mesh structure) 54 is located downstream from a gas-assisted spraying apparatus. The substrate-to-nozzle distance is approximately 20 mm and generally smaller than 100 mm.

The spraying apparatus preferably comprises at least a fluid channel, which may be formed by an embedded liquid tube and extends from fluid inlet 9 to outlet 15. A gas chamber having a central gas orifice 16 surrounds the fluid outlet so that an annular gap is formed between fluid 15 and gas orifice 16. The diameter of the annular gap is preferably smaller than 1 mm and the diameter of the fluid orifice 15 is generally 250 microns or less. One or more gas inlets 21, 22 are provided to supply the atomizing gas, which is expelled through gas orifice 16. The gas used to disintegrate the liquid may be chemically inert with respect to the fluid components. Suitable inert gases include nitrogen, and the like. Pressurized air represents an economical atomizing gas, which may be supplied using pressurized tanks or cylinders as well as compressors. The fluid is preferably fed using a high-accuracy pump to ensure precise control of the liquid supply. Depending on the molecular weight and concentration of the polymeric component to be atomized, an anti-clogging liquid (preferably a solvent for the non-volatile component) may be fed to avoid build-up or clogging of the orifices during the spraying process or during idle times.

A spray 57 is produced from a composition comprising at least a polymeric and a volatile component and a beneficial agent. The droplet size of the volatile component 155 is decreased at a relatively small distance "A" by at least 20 to 50%. Prior to deposition the concentration of nanometer-sized droplets within the spray preferably exceeds 10% and may reach more than 40% depending on the volatile component used. A plurality of fibers 150 are formed and directed in a controlled manner at comparatively low gas flow rates to the substrate 54. It is found that in order to fabricate a high-quality fibrous membrane extending in-between the openings of a tubular mesh structure, the polymer fibers should have a sufficient length ranging between approximately 15 to 500 microns and preferably be closely interconnected. Upon deposition on the mesh structure the polymer fibers 150 are in a near-dry state, since a major part of the solvent has evaporated. The remaining solvent ensures a good adhesion and tight connection of the fibers. The solvent is typically evaporated at low temperatures and preferably at ambient temperature to maintain the integrity and elasticity of the fibrous membrane.

A high voltage may be applied to charge the liquid composition so as to further control the deposition of the fibers on the substrate.

In order to manipulate the structure and/or surface properties of the fibrous membrane or scaffold, the velocity and impact angle of the produced fibers may be altered. This can be obtained by inducing an angular momentum into the emerging gas stream. The angular momentum influences the fiber trajectories 56 and promotes the inclination and interconnection of the fibers 150 on the substrate.

Furthermore, an additional gas stream surrounding the atomizing gas may be provided for enhanced control of the membrane formation process in terms of fiber diameter and membrane porosity. The temperature of the gas stream is generally higher than the ambient temperature and may range between 25 and 180 degree C. to increase the vapor pressure and enhance the evaporation of the volatile component.

The method of the present invention is particular suitable for the precise fabrication of self-supporting fibrous membranes or scaffolds for cell growing and/or implantation in a human or animal body, for fabricating small diameter synthetic vascular grafts or various drug delivery devices. Biomimic materials with good mechanical properties and homogeneous distributed surface features can be easily and reproducibly manufactured in one process step by processing various biodegradable and biostable polymers and fine-tuning the nano-micro structure (nano and micro fibers) of the membrane without the need of prolonged drying intervals.

Figure 6B:
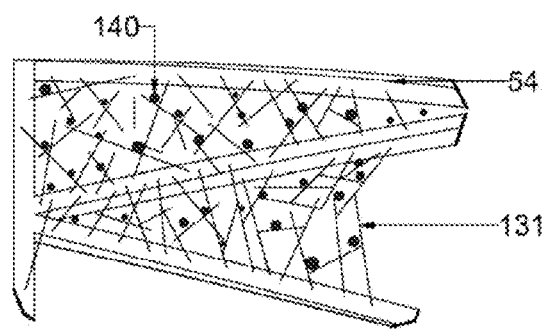
FIG. 6B is a schematic representation of an exemplary fibrous material.

FIG. 6B depicts a nano-micro textured material 131, which is comprised of polymer fibers and embedded particles 140 of a beneficial agent covering the surface of the mesh structure 54 including the openings. The material may be formed from a single layer or from several layers depending on the particular requirements in terms of permeability, thickness and strength. The formation of multiple textured layers is generally advantageous due to the improved connection between the fibers that Promote adhesion and mechanical integrity. The resulting fibrous material generally includes several surface features and may be fine-tuned in terms of wettability by manipulating the nano-micro structure of the coating in order to produce surfaces having improved wettability (hydrophilicity) and/or reduced wettability (hydrophobicity). Thus, the intrinsic hydrophilicity and hydrophobicity of the polymeric materials used may be fine-tuned to alter drug delivery and device biocompatibility.

Figure 7A:
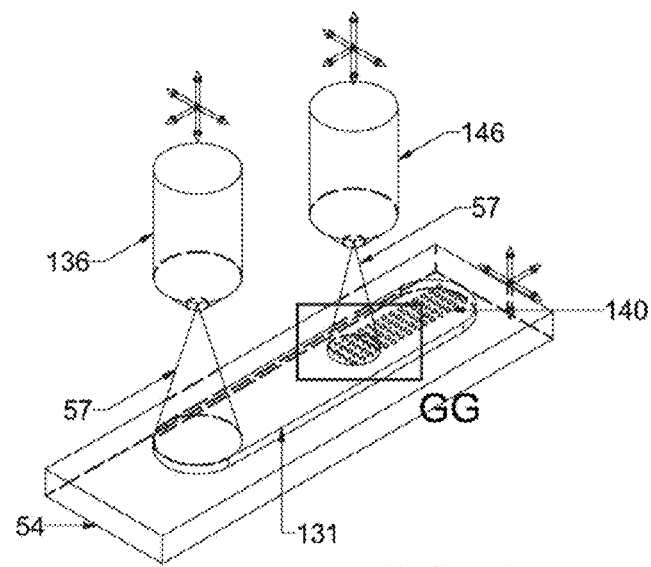
FIG. 7A is a schematic representation of the fabrication method of a drug-eluting fibrous material (three-dimensional polymer-drug matrix)
Figure 7B:
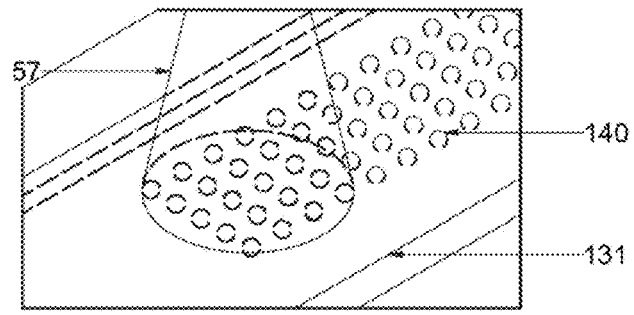
FIG. 7B is an extended view of a portion of FIG. 7A.
Figure 7C:
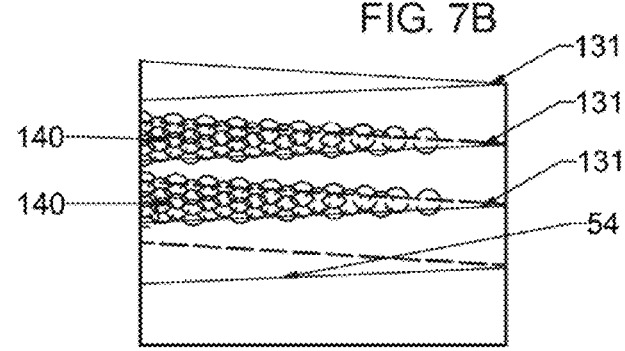
FIG. 7C is an isometric view of the fabricated polymer-drug matrix.

An exemplary setup and method to fabricate a drug-eluting fibrous membrane (three-dimensional matrix) and an exemplary three-dimensional matrix is depicted in FIG. 7A.

The three-dimensional matrix is produced by forming a polymeric layer 131 onto substrate 54 and dispensing or spraying a fluid containing a beneficial agent 140 onto layer 131. The process is repeated until the desired number of layers is deposited. The thickness of each layer may generally vary depending on the desired application. Layer 131 is fabricated by spraying a polymeric composition using a gas-assisted device 136 that preferably comprises means to promote solvent evaporation, such as an additional conditioned gas stream (not shown). The evaporation, fiber formation and transportation process is controlled so as to produce a near-dry polymeric layer that improves the adhesion of an additional layer of a drug dispersion or solution while minimizing diffusion of the drug into the polymer layer. Device 146 deposits the beneficial agent 140, which can be supplied in crystalline form (dry powder in a gaseous fluid or dispersion in a compatible liquid) and/or in the form of amorphous particles. The amount of beneficial agent or drug will depend upon the particular drug employed and medical condition being treated. If the beneficial agent comprises living cells specific compounds are preferably added to facilitate the survival of the cells and the operating conditions of the apparatus, such as the gas flow rate and temperature, should be adapted to prevent damage of the cells.

Devices 136, 146 may be moveable in X, Y and Z direction. Alternatively or in addition, a feed mechanism for moving the substrate in X, Y and Z direction may be provided. To deposit the beneficial agent precisely in various patterns, the devices 136, 146 and/or the substrate 54 are preferably aligned and moved in a three-dimensional way using a Cartesian or linear robot. In addition, multiple beneficial agents may be sprayed or dispensed simultaneously using multiple-fluid spraying and dispensing heads and the morphology of the drug can be fine-tuned in situ by providing an additional conditioned gas stream.

Thus, improved control of the spatial distribution of the embedded drug and drug release is provided while allowing the delivery of a variety of drugs having different release profiles. The three-dimensional matrix can be therefore easily adapted for a particular drug-delivery application and release profile so as to ensure controlled drug release in terms of release direction (prevent that drug enters blood flow) and release rate. For example, a three-dimensional polymer matrix may include a first layer having a decreased porosity and a hydrophil/lipophil balance preventing diffusion of the drug through the layer, a second layer having a relatively high surface area with pores comprising the drug, and one or more layers composed of materials like polymers, oils and/or vitamins for altering the release rate, solubility and/or shelf life of the drug.

Although some embodiments are shown to include certain features; the applicant specifically contemplate that any feature disclosed herein may be used together or in combination with any other feature on any embodiment of the invention. It is also contemplated that any feature may be specifically excluded from any embodiment of an invention. Many variations of the invention will occur to those skilled in the art.

The following examples are presented to illustrate the advantages of the present invention. These examples are not intended in any way otherwise to limit the scope of the disclosure.

Fabrication of Covered Stents

Stents made from Stainless Steel 316L having a diameter of 1.6 mm and a length of 14 and 20 mm were mounted on a holding device, as described in U.S. Pat. App. No. 60/776,522 and incorporated herein as a reference. Several compositions including biocompatible polymers and organic solvents were applied to the devices to form a fibrous membrane using the method of the present invention that will be described in more detail in the examples 1 to 3 below. For many polymers, physical properties, including fiber diameter, fiber alignment and pore dimension, can be regulated by controlling the composition of the solvent, the nozzle-substrate distance, the atomizing parameter, the level of fiber inclination, mandrel properties and the concentration, and/or degree of chain entanglements (viscosity) present in the starting solutions. When covering comparatively small medical implants such as arterial stents, the distance between fluid outlet and substrate should be generally larger than 20 mm to prevent disruption of the membrane by the atomizing gas. The distance should be smaller than 100 mm to minimize spreading of the spray cone and maintain acceptable transfer efficiencies. In this example, the spraying device has been aligned in relation to the stent and positioned at a distance of approximately 30 to 60 mm from the stent.

Since droplet size and velocity are an important factor influencing solvent evaporation and membrane formation, the droplet size and velocity should be relatively low. In the following examples, the initial median droplet size of the solvent fraction was around 3 microns at a distance of 10 mm downstream from the fluid orifice and was decreased by approximately 20% prior to deposition.

A syringe pump (Hamilton Inc., Reno, Nev., USA) was used to feed the fluid composition from a reservoir to the spraying device. The flow rate of the fluid composition may range between 0.5 ml/h and about 50 ml/h and the atomizing pressure between 0.5 bar to about 2.2 bar. Typically, a small amount of anti-clogging liquid may be supplied during the spraying operation to control the local environment around the liquid orifice and prevent solid build-up.

The composition was disintegrated at ambient temperature. During the application of the composition rotary motion was transmitted to the devices to rotate them about their central longitudinal axis. The devices were rotated at 130 rpm and translated along their central longitudinal axis along the spraying device at a translation speed of 2 mm/s and moved along the spraying device. Alternatively, spraying devices may be moved along the substrate. The coating process was continuously monitored using a spray diagnostic system, as described in US. Pat. App. No. 60/674,005 incorporated by reference herein, to monitor and control the atomization process.

Example 1

A polymer composition (composition A) was prepared from two biodegradable polymeric components. 5% by weight of a poly(lactide co glucolide) 50/50 copolymer and poly(ethylene glycol) was dissolved in acetone. A fibrous membrane was formed on several stents according to the method of the present invention. The membrane was applied in five passes. It could be seen that a layer with more homogeneous surface features was produced.

The stents were weighted before and after formation of the membrane and the measurement data were analyzed. As shown in Table 2 the average weight of the produced fibrous membranes was 233 μg and the coefficient of variation 11.8%.

TABLE 1

| Stent # | Membrane Weight [μg] |
|---|---|
| 1 | 265 |
| 2 | 217 |
| 3 | 259 |
| 4 | 228 |
| 5 | 200 |

TABLE 2

| Results | |
|---|---|
| Average | 233.8 |
| COV [%] | 11.8 |

Figure 10A:
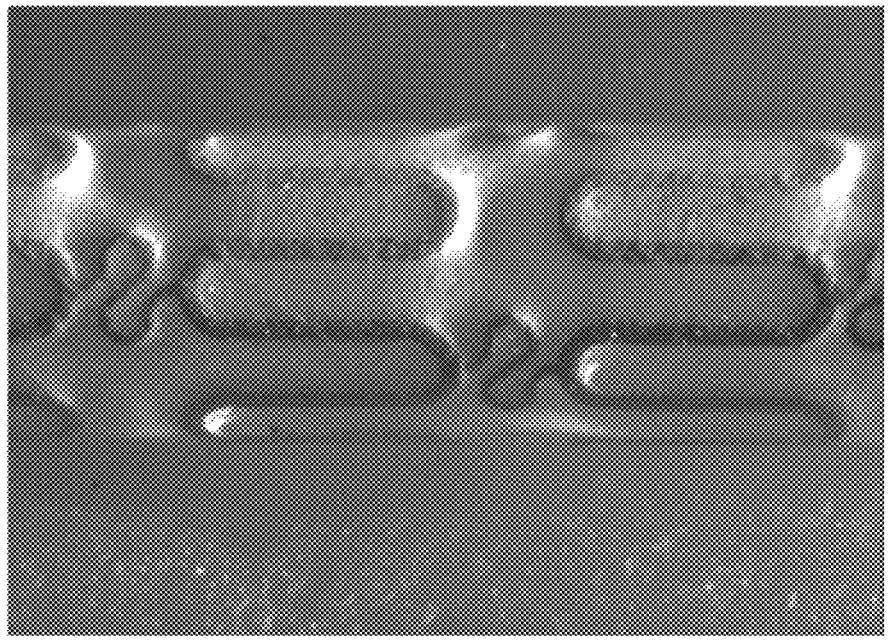
FIG. 10A is an image of a portion of a covered stent.
Figure 10B:
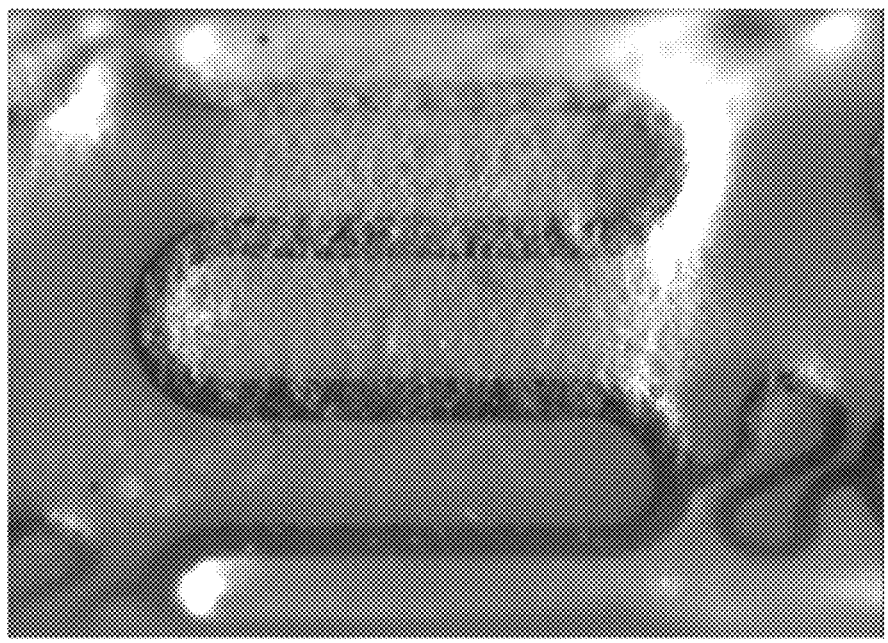
FIG. 10B is a magnified view of FIG. 10A.
Figure 10C:
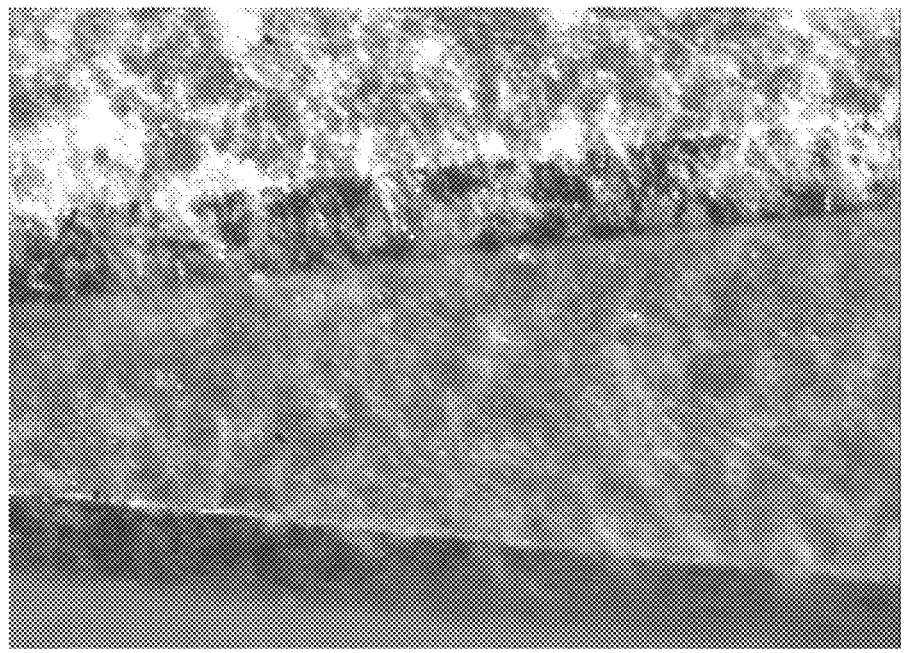
FIG. 10C is another image a portion of a covered stent.
Figure 10D:
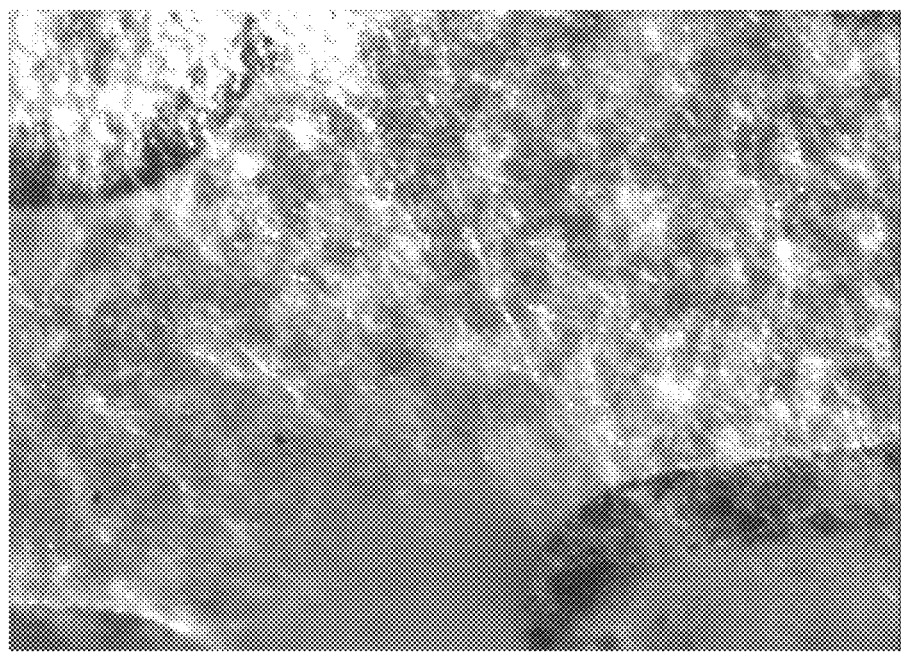
FIG. 10D is a magnified view of FIG. 10C.

The outer surface of the covered stents was inspected under a digital microscope and pictures were taken from a portion of the covered stent at different magnifications as shown in FIGS. 10A-10D. It can be seen that the fibrous layer covers the outer surface of the stent homogeneously. In FIG. 10C and FIG. 10D the surface features are visualized in more detail revealing an interconnected structure with small pores. The stent was expanded to test the elasticity and adhesion of the fibrous membrane and inspected under a microscope. It was found that the membrane adheres well. No defects were visible.

Example 2

A fibrous membrane composed of a biostable polymer composition was formed on cardiac stents. The polymer composition (composition B) was comprised of 2.5% by weight of poly(ethylene co vinyl acetate) with 40% Vinyl acetate dissolved in tetrahydrofuran.

Figure 8:
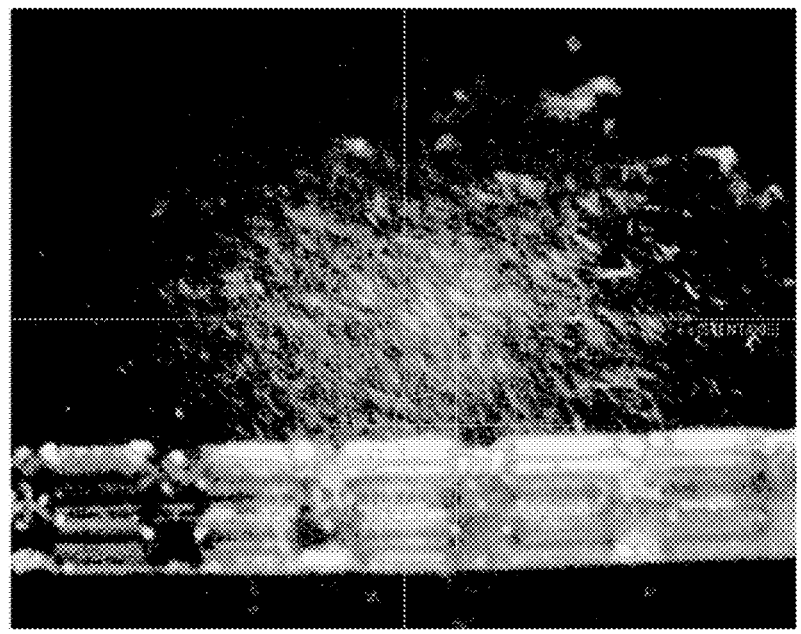
FIG. 8 is a screenshot of a fiber deposition process on a stent.
Figure 9:
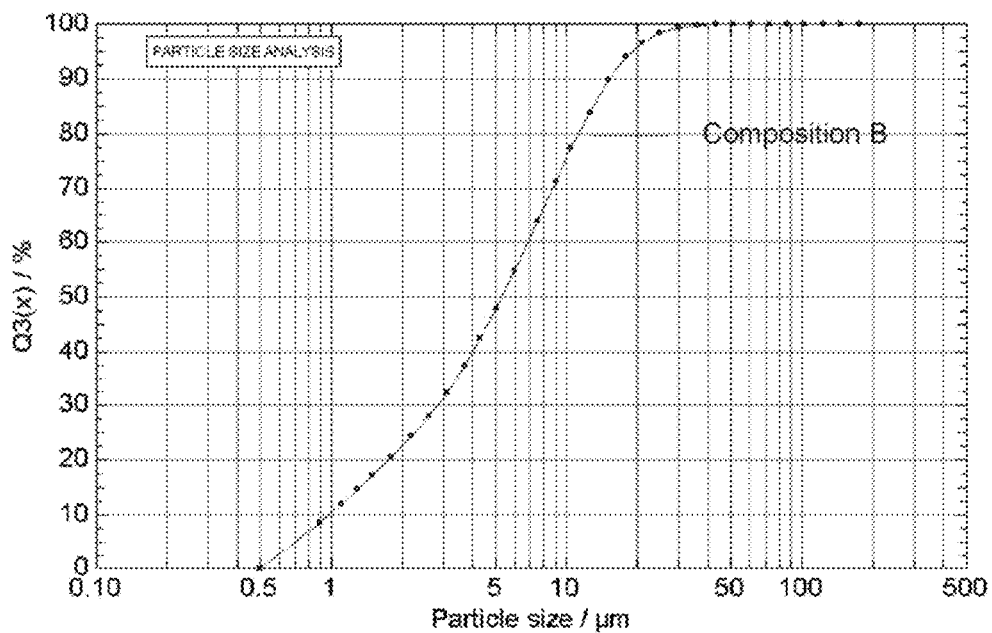
FIG. 9 is a size distribution of the fibers shown in FIG. 8.
Figure 11A:
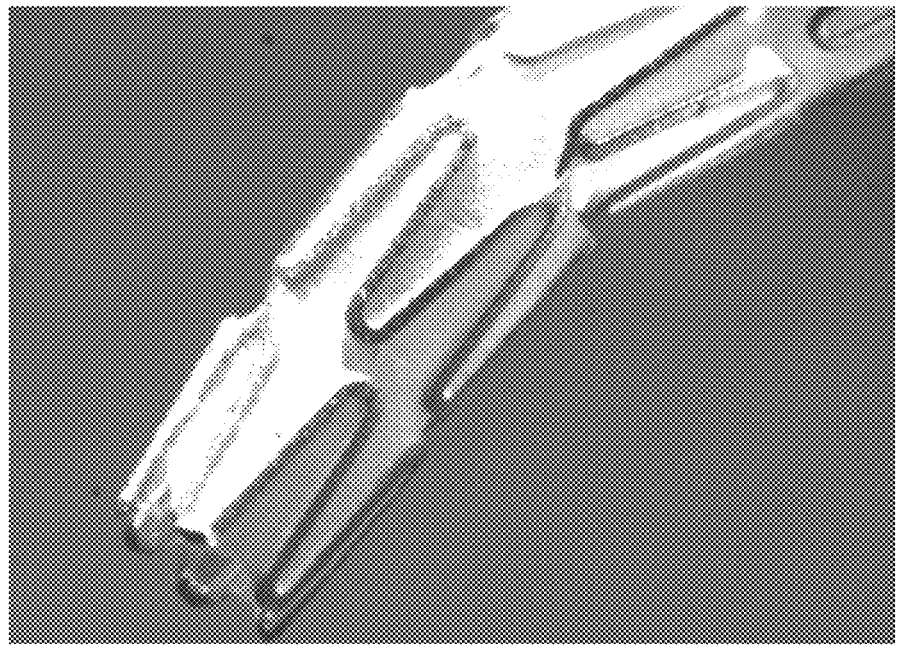
FIG. 11A is yet another image of a portion of a covered stent.
Figure 11B:
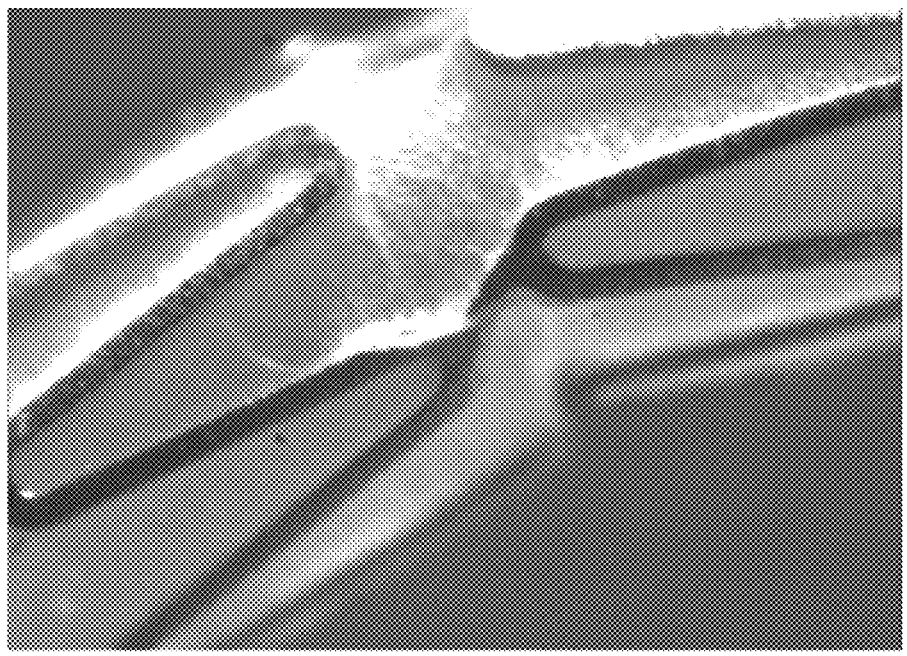
FIG. 11B is a magnified view of FIG. 11A.

The formation of the fibrous membrane was monitored and controlled using a spray diagnostic apparatus as described in US. Pat. App. No. 60/674,005. It was observed that the majority of the generated particles have a string or strand like shape, which were transported to the wire mesh (stent) so that a fibrous membrane was formed covering the openings of the wire mesh. FIG. 8 is a screenshot taken during the fiber deposition step on the stent. The size distribution of the fibers, which was measured prior to deposition, is displayed in FIG. 9. The outer surface of the covered stent was inspected under a digital microscope and pictures were taken from a portion of the stent at different magnifications as show in FIGS. 11A-11B. It can be seen that the outer surface including the openings of the stent was covered homogeneously. The stent was bent and expanded to demonstrate the elasticity and integrity of the membrane. No cracks or other defects were observed after mechanical deformation.

Example 3

A fibrous membrane composed of a biostable polymer composition was formed on cardiac stents. The composition (composition C) was composed of 2.5% by weight of poly(urethane) dissolved in tetrahydrofuran.

Figure 12A:
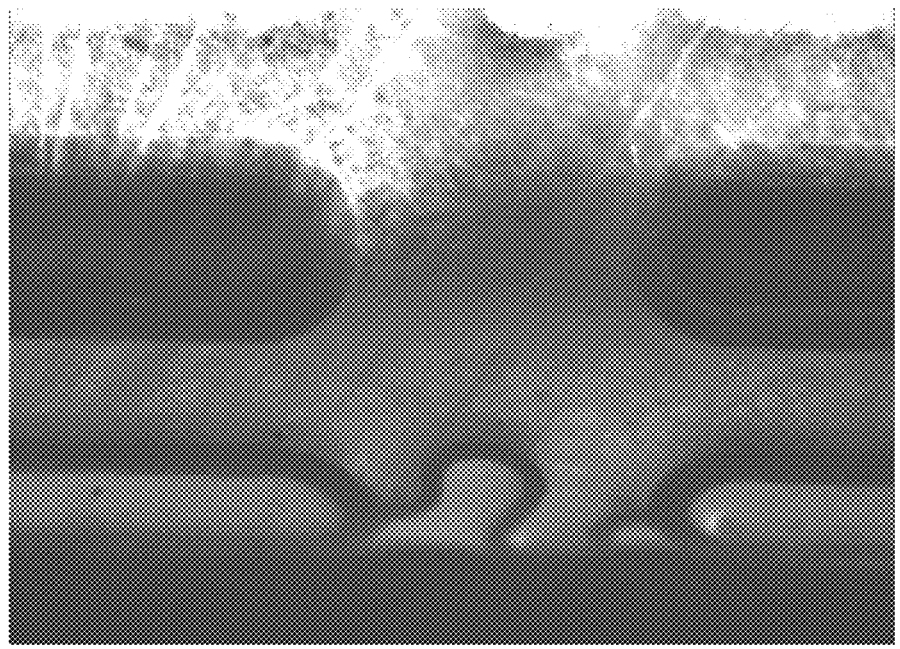
FIG. 12A is a further image of a portion of a covered stent.
Figure 12B:
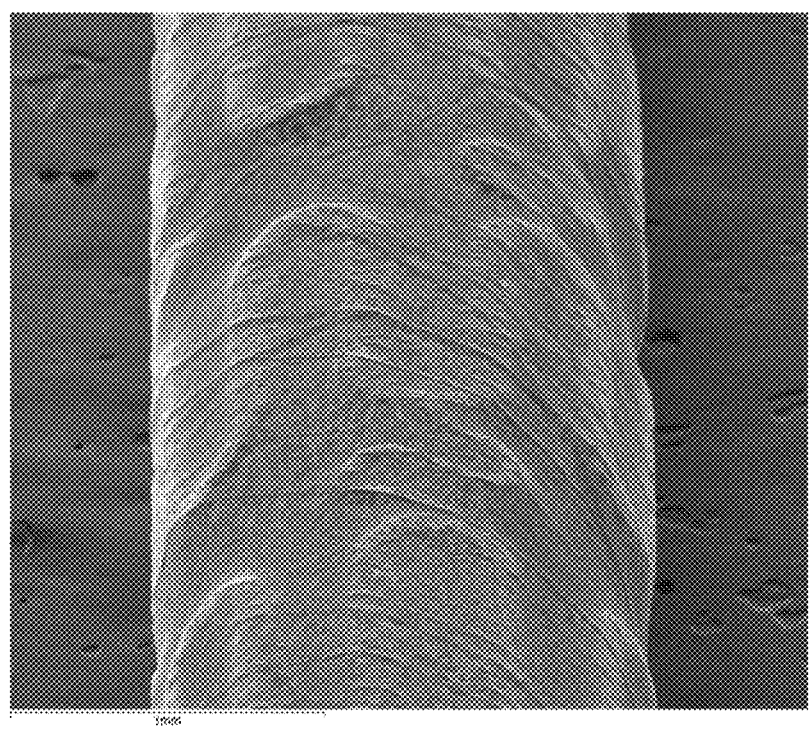
FIG. 12B is a magnified view of FIG. 12A.
Figure 12C:
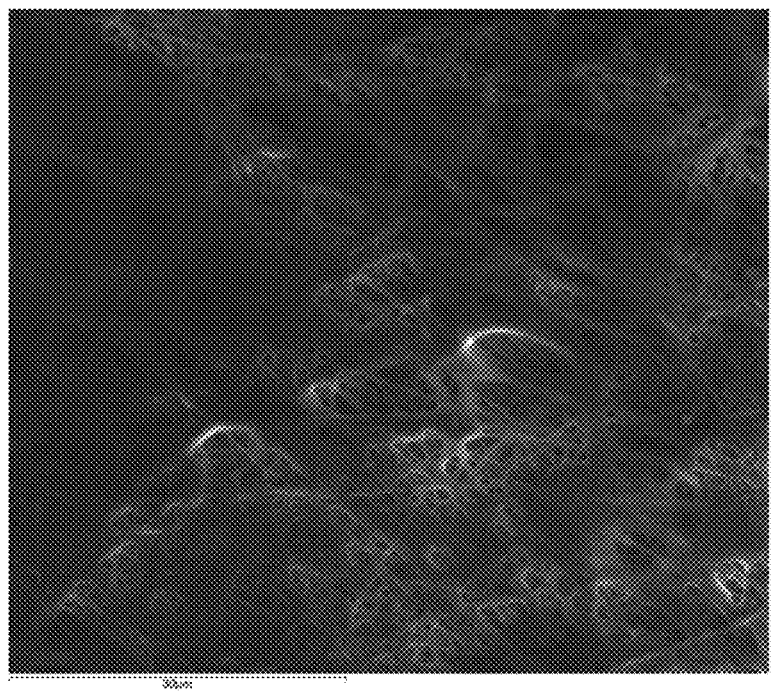
FIG. 12C is a SEM image.
Figure 12D:
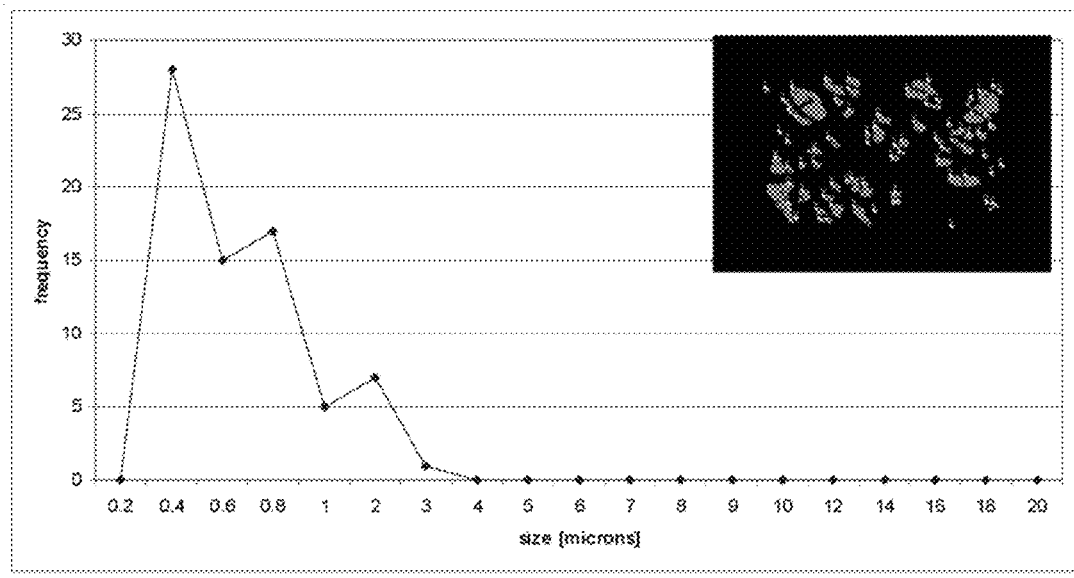
FIG. 12D is a surface feature analysis of FIG. 12C.

After formation of the membrane the covered stents were inspected under a digital microscope. FIG. 12A and FIG. 12B are micrographs of a portion of a stent visualizing the micro porous structure of the fibrous layer. In FIG. 12C a portion of the fibrous layer covered stent is depicted in more detail. The surface is visualized by scanning electron microscopy (SEM) at a magnification of 1500×. Nanofibers are visible. The nano-micro features including a plurality of small pores are clearly visible on the entire surface of the stent. The size of the features was determined using an image analysis technique. FIG. 12D shows a binary image computed from the micrograph of FIG. 12C and a chart showing the size of the surface features. The feature size ranges between 200 nm and 4 microns with a peek at 400 nm.

The results indicate that non-woven fibrous materials with good mechanical integrity can be reproducibly produced from various biodegradable and biostable polymers using the method of the present invention. The materials are composed of nano-scale to micron-scale diameter fibers, a size-scale that approaches the fiber diameters observed in the native extracellular matrix. Thus, biomimicry-inspired materials for better cell and tissue growth and/or prevention of adverse body reactions such as inflammation and unwanted cell proliferation (smooth muscles cells) may be produced.

A flexible and innovative approach is provided to design three-dimensional materials having a determined fiber thickness, length, inclination, and interconnection. Multiple drugs having various drug loads and drug morphologies (crystalline and/or amorphous) can be easily embedded in a spatially controlled position. The method of the present invention allows for fine-tuning the polymer matrix and drug morphology to obtain a desired drug release. It combines the advantage of drug load and film thickness flexibility with precise dosage control and ability to design complex drug release profiles.

The invention claimed is:

1. Fibrous non-woven polymeric material, wherein the material is composed of a plurality of closely interconnected short fibers having a diameter in the nano-micrometer range, being inclined with respect to each other and the material is a three-dimensional structure; and wherein the material is manufactured using a pneumatic spraying method comprising the following steps:
   a. providing an atomizing device;
   b. providing a substrate;
   c. supplying to the atomizing device at least a liquid composition including at least a volatile solvent component and at least a non-volatile polymeric component wherein the volatile solvent component is a solvent for the non-volatile polymeric component;
   d. atomizing the liquid composition by supplying an atomizing gas stream to the atomizing device to form droplets smaller than 10 microns in diameter of the solvent component and evaporating the solvent component to cause the polymeric component to undergo at least a partial solidification and forming a plurality of discrete fibers comprising the polymeric component having a length of 15 to 500 microns and a diameter in the nano-micrometer range; and wherein at least 10% of all fibers have a length of more than 15 microns; and e. depositing the fibers on the substrate so that a mesh structure composed of a plurality of interconnected short fibers is formed, and the fibers are in a near-dry state and remaining solvent ensuring a good adhesion and tight connection of the fibers.

2. The material according to claim 1, further comprising the step of inducing swirl motion in the atomizing gas stream to control the inclination and orientation of the fibers.

3. The material according claim 1, wherein the velocity of the atomizing gas exceeds sonic speed and at least 20% of the droplets formed from the volatile component are submicron in diameter.

4. The material according to claim 1, further comprising the step of providing an additional gas stream to increase temperature of the atomizing gas stream to a temperature higher than ambient temperature.

5. The material according to claim 1, further comprising the step of applying an electrical charge to the liquid composition to control deposition of the fibers.

6. The material according to claim 1, wherein the liquid composition comprises a therapeutic agent.

7. The material according to claim 1, wherein the substrate is a scaffold.

8. The material according to claim 7, further comprising the step of removing the material from the scaffold.

9. The material according to claim 1, wherein the substrate is tissue of a living body, and the non-woven polymeric material is formed to cover at least a part of the tissue surface.

10. The material according to claim 1, wherein the substrate is a medical device and the non-woven polymeric material covers at least a part of the medical device.

11. The material according to claim 10, wherein the medical device is a stent consisting of an expandable tubular hollow mesh structure having openings and the material covers the openings of the mesh structure.

12. The material according to claim 1, further comprising the step of applying a therapeutic agent using an additional atomizing device after at least a partial solidification of the polymeric component is initiated to allow spatially defined embedding of the therapeutic agent into the non-woven polymeric material.

13. The material according to claim 1, wherein the material is biodegradable.

14. The material according to claim 1, wherein the material mimics the size scales of fibers composing the extracellular matrix.

15. The material according to claim 1, wherein the material is comprised of multiple layers in which one or more therapeutic agents are embedded.

16. The material according to claim 1, wherein the material comprises one or more therapeutic agents or cells.

17. The material according to claim 1, wherein distance between fluid outlet of the atomizing device and the substrate is larger than 20 mm to prevent disruption of the material by the atomizing gas stream.

18. The material according to claim 1, wherein the material forms a synthetic vascular graft for implantation in a human or animal body.

19. The material according to claim 1, wherein the material is in the form of self-supporting scaffold from which the substrate has been removed.

* * * * *